United States Patent
Kontiola

(10) Patent No.: US 9,462,947 B2
(45) Date of Patent: Oct. 11, 2016

(54) MEASUREMENT METHOD AND ARRANGEMENT UTILIZING ELECTROMAGNETIC WAVES

(71) Applicant: PHOTONO OY, Helsinki (FI)

(72) Inventor: Antti Kontiola, Helsinki (FI)

(73) Assignee: PHOTONO OY, Helsinki (FI)

(*) Notice: Subject to any disclaimer, the term of this patent is extended or adjusted under 35 U.S.C. 154(b) by 0 days.

(21) Appl. No.: 14/785,603

(22) PCT Filed: Apr. 17, 2014

(86) PCT No.: PCT/FI2014/050287
§ 371 (c)(1),
(2) Date: Oct. 19, 2015

(87) PCT Pub. No.: WO2014/170556
PCT Pub. Date: Oct. 23, 2014

(65) Prior Publication Data
US 2016/0066786 A1    Mar. 10, 2016

(30) Foreign Application Priority Data

Apr. 19, 2013 (FI) .................................. 20135401

(51) Int. Cl.
| | |
|---|---|
| A61B 3/10 | (2006.01) |
| A61B 3/14 | (2006.01) |
| A61B 3/00 | (2006.01) |

(Continued)

(52) U.S. Cl.
CPC .............. *A61B 3/165* (2013.01); *A61B 3/102* (2013.01); *A61B 3/1005* (2013.01); *A61B 3/107* (2013.01); *A61B 5/0066* (2013.01); *A61B 5/0095* (2013.01)

(58) Field of Classification Search
USPC .................................................. 351/200–246
See application file for complete search history.

(56) References Cited

U.S. PATENT DOCUMENTS

| | | |
|---|---|---|
| 6,110,110 A | 8/2000 | Dublin, Jr. et al. |
| 6,671,043 B1 | 12/2003 | Huettman |

(Continued)

FOREIGN PATENT DOCUMENTS

| | | |
|---|---|---|
| DE | 3918629 A1 | 12/1990 |
| DE | 10 2008 049 692 A1 | 4/2010 |

(Continued)

OTHER PUBLICATIONS

International Search Report (PCT/ISA/210) mailed on Aug. 5, 2014, by the European Patent Office as the International Searching Authority for International Application No. PCT/FI2014/050287.

(Continued)

*Primary Examiner* — Mohammed Hasan
(74) *Attorney, Agent, or Firm* — Buchanan Ingersoll & Rooney PC

(57) ABSTRACT

A method is disclosed for measuring pressure under a flexible cover by utilizing electromagnetic waves. Laser radiation is directed to the cover from a distance to generate vibration or a mechanical wave at the cover at at least one generation location of the cover on the basis of photoacoustic phenomena. Based on the electromagnetic waves, cover vibrations are detected due to the mechanical wave, and recorded to detect the mechanical wave at at least one recording location and to form mechanical wave information. Pressure information of pressure under the flexible cover is detected based on at least one recorded signal.

18 Claims, 1 Drawing Sheet

(51) Int. Cl.
*A61B 3/16* (2006.01)
*A61B 5/00* (2006.01)
*A61B 3/107* (2006.01)

(56) References Cited

U.S. PATENT DOCUMENTS

| | | |
|---|---|---|
| 2003/0187342 A1 | 10/2003 | Cuzzani et al. |
| 2005/0279369 A1* | 12/2005 | Lin .................. A61F 9/008 128/898 |
| 2008/0255433 A1 | 10/2008 | Prough et al. |
| 2009/0292202 A1 | 11/2009 | Presura et al. |
| 2010/0249562 A1 | 9/2010 | Zhang et al. |
| 2010/0249569 A1 | 9/2010 | Jinde et al. |
| 2012/0150013 A1 | 6/2012 | Peyman |
| 2012/0302862 A1 | 11/2012 | Yun et al. |
| 2013/0085370 A1 | 4/2013 | Friedman et al. |
| 2013/0109947 A1 | 5/2013 | Wood |
| 2014/0148658 A1 | 5/2014 | Zalevsky et al. |
| 2015/0085249 A1* | 3/2015 | Abreu ............... A61B 3/1241 351/205 |

FOREIGN PATENT DOCUMENTS

| | | |
|---|---|---|
| WO | WO 2006/067699 A1 | 6/2006 |
| WO | WO 2010/031395 A1 | 3/2010 |
| WO | WO 2012/101644 A1 | 8/2012 |
| WO | WO 2013/063540 | 5/2013 |

OTHER PUBLICATIONS

Written Opinion (PCT/ISA/237) mailed on Aug. 5, 2014, by the European Patent Office as the International Searching Authority for International Application No. PCT/FI2014/050287.
Finnish Search Report for FI 20135401 dated Feb. 4, 2014 (3 pages).
"Thermoacoustic imaging", Wikipedia article [online], Nov. 3, 2011, http://en.wikipedia.org/w/index.php?title=Thermoacoustic_imaging&oldid=458756500, 4 pages.
Office Action (Opinion on Patentability) issued on Apr. 18, 2016, by the Finnish Patent Office in corresponding Finnish Patent Application No. 20135401. (6 pages).

* cited by examiner

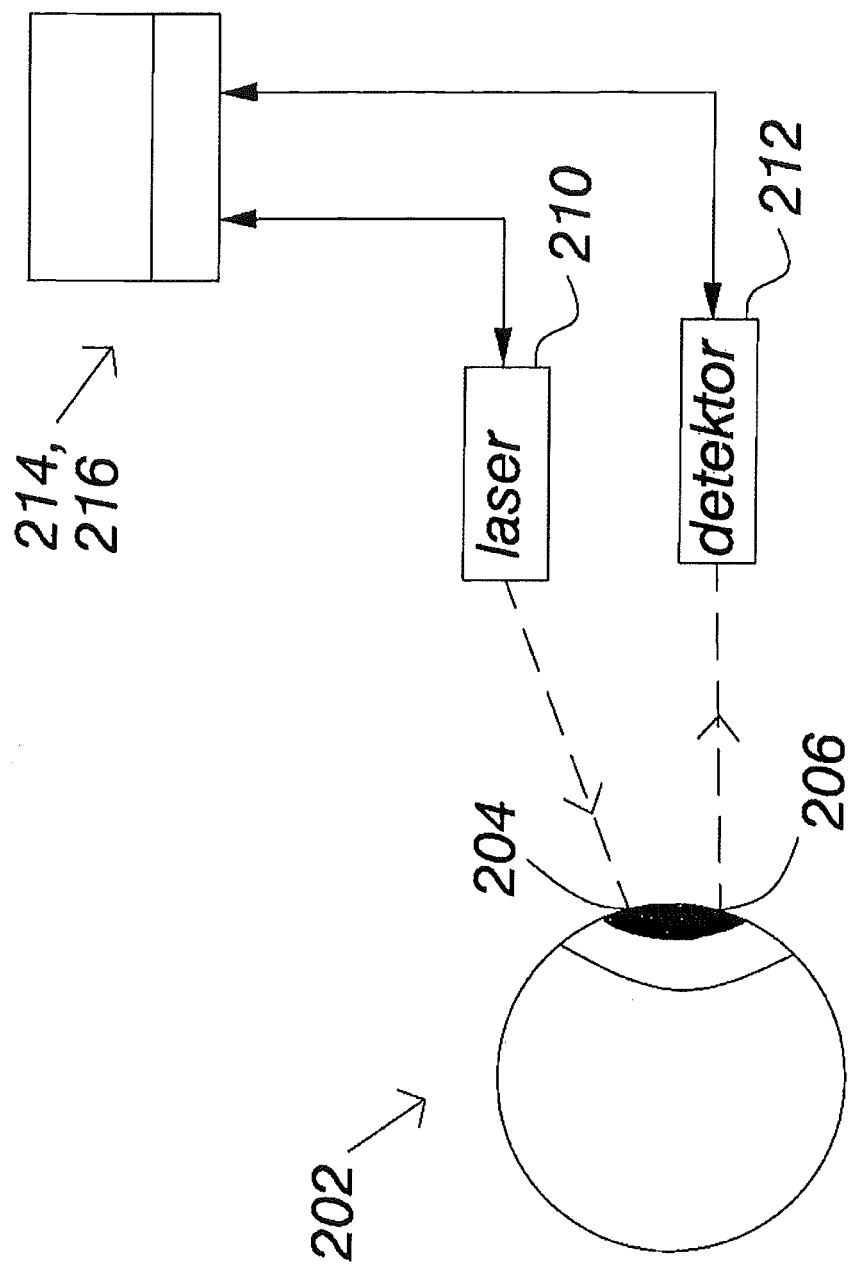

MEASUREMENT METHOD AND ARRANGEMENT UTILIZING ELECTROMAGNETIC WAVES

THE FIELD OF THE INVENTION

The invention relates to measurement of physical eye properties by utilizing photo-acoustic (PA) excitation of electromagnetic wave signals in eye.

THE STATE OF THE ART

Essentially, the excitation and/or detection of electromagnetic wave signals is to be performed by means of a beam of electromagnetic wave or impulse waveform, produced e.g. by a laser or pulsed laser source, which is for example mediated via electromagnetic waveguide (e.g. an optical fibre, collimator, lenses, masks and/or an arrangement of mirrors) and targeted onto an eye of a patient. An input of the electromagnetic wave into the eye is followed by electro-magnetic-mechanical conversion (e.g. photo-acoustic conversion) which generates heat and mechanical vibration into the eye tissue. Correspondingly, at an output of electromagnetic waves, mechanical vibrations of the eye tissue are detected (e.g. by means of optical interferometry, optical coherence tomography or laser Doppler vibrometry). The objective is thereby to generate mechanical waves (e.g. ultrasonic waves) to the eye and to detect said waves from the eye. The potential applications relate especially to determination of an intraocular pressure, i.e. an eye pressure.

Intraocular pressure measurement is one of the key measurements in ophthalmology, because glaucoma disease is a leading cause of blindness in western countries. Higher intraocular pressure is considered to be one of the key factors in pathophysiology of glaucoma.

In US patent application US 2010/0249569A1 is presented a non-contact ultrasonic tonometer for intraocular pressure measurements, in which is used piezo-electrical transducers to perform excitation of frequency signals into the eye. The positions of said transducers have to be exactly measured, which causes complexity and slowness to the intraocular pressure measurement procedure. Also temperature variations can be error sources in the intraocular pressure measurement information together with possible errors in said position measurements.

SHORT DESCRIPTION OF THE INVENTION

The object of the present invention is to accomplish an improved pressure measurement method and arrangement being accurate and practical to use in pressure measurement applications. This is achieved by a method for measuring pressure under a flexible cover by utilizing electromagnetic waves. In the method laser radiation is directed to the cover from a distance to generate vibration or mechanical wave to the cover at at least one generation location in the cover on the basis of photoacoustic phenomena, the generation location being at least one point where the laser radiation hits the cover, and in the method is detected on the basis of electromagnetic waves cover vibrations due to the mechanical wave, is recorded the detected mechanical wave at at least one recording location to form mechanical wave information, and in the method is determined pressure information of pressure under the flexible cover based on at least one recorded signal.

An object of the invention is also an arrangement for measuring pressure under a flexible cover by utilizing electromagnetic waves. The arrangement comprises means for forming and directing laser radiation to the cover from a distance to generate vibration or mechanical wave to the cover at at least one generation location in the cover on the basis of photoacoustic phenomena, the generation location being at least one point where the laser radiation hits the cover, and means for detecting on the basis of electromagnetic waves cover vibrations due to the mechanical wave, means for recording the detected mechanical wave at at least one recording location to form mechanical wave information, and means for determining pressure information of pressure under the flexible cover based on at least one recorded signal.

The invention is based on utilization of vibration or mechanical wave to a cover generated by laser radiation to at least one generation location in the cover on the basis of photoacoustic phenomena. In the invention is detected on the basis of electromagnetic waves cover vibrations due to the mechanical wave, and recorded the detected mechanical wave at at least one recording location to form mechanical wave information on the basis of which is determined pressure information of pressure under the flexible cover.

The benefit of the invention is that error sources related to pressure measurements are minimized because distance information is not relevant and because the invention is not sensitive to temperature variations in human body measurements e.g. in intraocular pressure measurements or in blood pressure measurements. Thus the invention enables practical and fast pressure measurements which have less error sources than prior art measurements.

SHORT DESCRIPTION OF FIGURES

FIG. 1 presents a preferred embodiment according to the present invention.

DETAILED DESCRIPTION OF THE INVENTION

In FIG. 1 is presented schematically an arrangement according to the present invention for measuring pressure under a flexible cover 202 by utilizing electromagnetic waves. In the arrangement is formed and directed laser radiation to the cover 202 from a distance 200 to generate vibration or mechanical wave to the cover 202 at at least one generation location 204 in the cover on the basis of photoacoustic phenomena. The generation location is at least one point 206 where the laser radiation hits the cover 202. The laser radiation is formed and directed by means 210, which comprise for example laser diodes and focusing and directing means to form and direct the laser radiation preferably to a scale of different frequencies. The means 210 can generate the mechanical wave for example by tuning at least one of centre frequency and pattern of the mechanical wave to facilitate an in vivo excitation through the cover (202).

The arrangement of FIG. 1 comprises means 212 for detecting on the basis of electromagnetic waves cover vibrations due to the mechanical wave and means 214 for recording the detected mechanical wave at at least one recording location to form mechanical wave information. In some embodiments of the invention the distance of said at least one recording location 206 from said at least one generation location 204 is known for example by being fixed in the arrangement or by distance measurement(s). The means 212 can be constructed for example by using at least one of optical interferometry device, optical coherence tomography device and laser Doppler vibrometry device.

The means 212 can detect cover 202 vibrations for example based on the detection of first arriving signal (FAS).

The arrangement of FIG. 1 further comprises means 216 for determining pressure information of the pressure under the flexible cover 202 based on the recorded signal(s). The means 214 and 216 can be realized by one or more preferably digital processor(s). In the example of FIG. 1 the means 214, 216 are located in a same computer unit 214, 216.

In one embodiment according to the invention pressure under a flexible cover 202 is intraocular pressure, and the flexible cover 202 is surface 202 of an eye. The arrangement according to the invention can also comprise means for measuring at least one of curvature of the eye, thickness of a cornea of the eye and water content of the eye to form additional measurement information to be utilized in the determination of the intraocular pressure information.

In another embodiment according to the invention pressure under a flexible cover 202 is blood pressure, and the flexible cover 202 is wall 202 of a blood vessel. Blood pressure is one of the most important parameters in emergency and intensive care units treating critically ill or injured patients. Also chronic elevated blood pressure is one of the pathophysiological factors causing arterial diseases, stroke and myocardial infarct.

Laser radiation excitation can be performed by different frequencies to the eye 202 or to the blood vessel 202 or to other flexible cover 202 of the embodiments according to the invention in order to obtain vibration and/or resonance information in different frequencies for the determination of pressure information of eye or blood vessel or other flexible cover. Thus frequency response information can be utilized in the pressure information determination with or without velocity information of mechanical wave (e.g. ultrasound wave) in the eye 202 or in the blood vessel 202 or under or in other flexible cover 202.

Next will be discussed related to FIG. 1 a more detailed preferred embodiment according to the present invention, said embodiment being especially related to eye pressure, i.e. intraocular pressure measurements. By means 210 is generated by utilizing electromagnetic waves at least one mechanical wave at at least one generation location 204 into the eye tissue. The eye 202 can be open or closed. Measurement can be made from cornea or sclera of the eye. The preferred arrangement comprises means 212 for detecting the electromagnetic output. In said detection is detected by means of electromagnetic waves eye tissue vibrations due to at least one mechanical wave. In a preferred phase delayed embodiment laser beam is guided through an optical fiber where after it is absorbed to the eye tissue and generates for example an ultrasound wave. Time-delayed excitation is attained by employing a time delay ($t_0$) between trigger signals of for example laser diodes.

The arrangement comprises means 214 for recording the detected at least one mechanical wave at at least one recording location to form mechanical wave information. Distance of said at least one recording location from said at least one generation location is known. The arrangement comprises means 216 for determining intraocular pressure based on at least one recorded signal. Said means 214, 216 are arranged for example in a computer processor utilizing calculative programs, when needed. The computer processor 214, 216 is presented schematically in the FIG. 1. Wired or wireless data transmission is used between the computer processor 214, 216 and the means 210, 212 to perform data transmissions between them.

In the method according to the preferred embodiment is generated by means of electromagnetic waves at least one mechanical wave at at least one generation location into the eye 202 directly or through an eyelid. In the second method step is detected by means of electromagnetic waves ocular vibrations due to at least one mechanical wave, is recorded the detected at least one mechanical wave at at least one recording location to form mechanical wave information, and distance of said at least one recording location from said at least one generation location is known, and further in the second method step is determined eye properties based on at least one recorded signal. If the recorded signal is analyzed based on signal amplitude in different frequencies, said distance information and/or location information is not necessarily relevant.

Different frequencies can be used. The preferred arrangement can also comprise means 100 for tuning at least one of centre frequency and pattern of the mechanical wave to facilitate an in vivo excitation into the eye 202. The second means 103 for detecting (FIG. 2) by means of electromagnetic waves ocular vibrations comprise at least one of a optical interferometer 103, optical coherence tomography device 103 and laser Doppler vibrometer 103, and correspondingly the detection of ocular vibrations is based on at least one of optical interferometry, optical coherence tomography and laser Doppler vibrometry. The optical interferometer 103, optical coherence tomography device 103 and laser Doppler vibrometer 103 can also be named as electromagnetic wave sensors 103. The preferred detection of ocular vibrations by the second means 103 is based on the detection of at least one of first arriving signal (FAS). Eye can be excited to different frequencies and the amplitude of the mechanical wave detected. Different intraocular pressures output different pattern of amplitudes at different frequencies. Used frequencies can be for example ultrasound frequencies or lower frequencies such as even infrasound frequencies.

In following description is described in details one of the preferred modes of the present invention. Photo-acoustic (=PA, later on in this description) means, i.e. electromagnetic wave sensors, essentially enable flexible tuning of the excitation and detection which, by a number of ways, can facilitate the in vivo excitation and detection of vibrations of the surface of the eye. The idea is to generate a mode that is strong and easy to recognize at the receiver. This mode should also be able to differentiate between intraocular pressures.

Tuning of excitation and/or detection by PA can be comprised of the following aspects: A. Tuning of optical wavelength (wavelength of the electromagnetic beam) so as to provide maximal light absorption in the eye conditioned on minimizing the absorption in the covering soft tissue. The photoacoustic source (i.e. source of mechanical waves) is thereby generated into the eye. B. Tuning of the shape of an illuminated surface so as to produce the strongest possible targeted mode at the receiver. Optimal shape can be, e.g., a sphere, line or crest. C. Tuning of the mechanical (e.g. ultrasonic) centre frequency of excitation, so as to provide (a) optimal excitability and (2) sufficient (or optimal) sensitivity to intraocular pressure. D. Tuning of the magnitude of phase delay in the case of phase delayed excitation, so as to facilitate selective excitation of one particular mode.

1. Photoacoustic (PA) means (e.g. optical fibre and/or lasers diodes) enables to increase the number of sources due to a smaller element diameter. The accuracy of assessment of vibration or the accuracy of assessment of mechanical wave velocity can thus be increased.

2. Position of the photo-acoustic source or an array of photo-acoustic sources can easily be scanned, so as to further increase the accuracy of velocity determination.
3. PA means can enable rapid tuning of the acoustic centre frequency of excitation, so as to enable assessment of dispersion of the first arriving signal (FAS) velocity, successively from rapidly iterated measurements by scanning the centre frequency.
4. Proper choice of the optical wavelength to minimize optical absorption in the eyelid in case the measurement is performed through the eyelid. The lower the optical absorption the weaker the PA source is. When the PA source is weak in the soft tissue, energy excited into interference modes in the soft tissue is also weak.
5. Proper choice of the optical wavelength to minimize optical scattering, so as to enable sharp beam towards the eye.
6. Proper choice of optical wavelength to maximize the optical absorption in the eye, so as to produce a strong PA source to the eye.
7. Proper tuning of the acoustic excitation frequency, so as to facilitate the excitation of A0 through the soft tissue coating. The A0 is most efficiently excited at very low ultrasonic frequencies, preferably at 20-120 kHz, however, piezo elements of such frequencies have inappropriately large diameter for the purpose. PA means enable point sources at such frequencies.
8. In the method and arrangement according to the present invention is preferably properly adjusted the shape and size of area irradiated by the laser (preferably a narrow line), so as to maximize the amount of photoacoustic energy within the safety limits for the human tissue, but to minimize the surface area to facilitate the excitation into the eye. The excitation power is a function of the beam intensity and the surface area irradiated.
9. Phase delayed excitation by an array of sources can be used to further facilitate the excitation of A0.
10. Implementation of a point or narrow line detector, also enabled by PA means.
11. Important features are convenient position adjustments and appropriate feedback based on the ultrasound signal being measured during the fine adjustments of the position. The main requirements are reasonably rapid and reproducible positioning.
12. According to the experience from present US devices, a hand-held probe together with instant response from the measured signal enable intuitive positioning.
    Alternatively, the PA source can be packed together with one or two PA receivers inside a hand-held probe, wherein the source is implemented by a laser diode or an array of laser diodes and the receiver by, e.g., a pair of interferometric detectors. Such a design can provide a potential embodiment for the entire photoacoustic (PA) device, which is suitable for clinical use.
13. If measurements are made through for example an eyelid it may be preferred to carefully choice several parameters (such as for example optical wavelength and beam intensity, tuning the PA source for optimal acoustic wavelength, and potentially hampering the propagation of interference modes) simultaneously or partly simultaneously.
14. A means enable flexible tuning of the excitation (and detection).
    a. Point or point-like (including thin line) sources are enabled also at very low frequencies (f=20-120 kHz). PA means also enable implementation of point-like detectors. The point-like source and receivers are known to be optimal for facilitating the excitation and detection.
    b. Instantaneous tuning of the centre frequency of ultrasonic excitation by certain PA sources (laser diodes), so as to enable dispersion assessment of transient ultrasound modes (such as the FAS).
    c. Phase-delayed excitation to further facilitate the excitation of ultrasonic modes. Advantages of PA arise from the possibility to point-like sensor elements, which enable inclusion of several sensor elements inside a short clinical array probe.
15. Device design which may be of critical importance for the success with clinical applications of the method proposed.

Although the invention has been presented in reference to the attached figures and specification, the invention is by no means limited to those, as the invention is subject to variations within the scope allowed for by the claims.

The invention claimed is:

1. A method for measuring intraocular pressure under a surface of an eye by utilizing electromagnetic waves, comprising:
    directing laser radiation to the surface from a distance to generate vibration or a mechanical wave at the surface at at least one generation location of the surface based on a photoacoustic phenomena, the generation location being at least one point where the laser radiation hits the surface;
    detecting, based on electromagnetic waves, surface vibrations due to the mechanical wave by using at least one of optical interferometry, optical coherence tomography and laser Doppler vibrometry;
    recording detected surface vibrations at at least one recording location to form mechanical wave information; and
    determining pressure information of intraocular pressure under the surface of the eye based on at least one recorded signal of the recording location.

2. A method according to claim 1, comprising:
    measuring at least one of curvature of an eye, thickness of a cornea of an eye and water content of an eye to form additional measurement information for determining intraocular pressure information.

3. A method according to claim 2, wherein a distance of said at least one recording location from said at least one generation location is known.

4. A method according to claim 3, wherein the detecting of surface vibrations is based on a detection of a first arriving signal (FAS).

5. A method according to claim 4, comprising:
    generating the mechanical wave by tuning at least one of a centre frequency and a pattern of the mechanical wave to facilitate an in vivo excitation through the surface.

6. A method according to claim 1, wherein a distance of said at least one recording location from said at least one generation location is known.

7. A method according to claim 1, wherein the detecting of surface vibrations is based on a detection of a first arriving signal (FAS).

8. A method according to claim 1, comprising:
    generating the mechanical wave by tuning at least one of a centre frequency and a pattern of the mechanical wave to facilitate an in vivo excitation through the surface.

9. A method according to claim 1, wherein the generation location is a cornea or schlera of an eyeball.

10. A method according to claim 1, wherein the generation location is a cornea or schlera of an eyeball.

11. An arrangement for measuring intraocular pressure under a surface of an eye by utilizing electromagnetic waves, the arrangement comprising:
means for forming and directing laser radiation to a surface from a distance to generate vibration or a mechanical wave at the surface at at least one generation location of the surface based on photoacoustic phenomena, the generation location being at least one point where the laser radiation hits the surface;
means for detecting, based on electromagnetic waves, surface vibrations due to the mechanical wave by using at least one of an optical interferometer, an optical coherence tomography device and a laser Doppler vibrometer;
means for recording detected surface vibrations at at least one recording location to form mechanical wave information; and
means for determining intraocular pressure under surface of an eye based on at least one recorded signal of the recording location.

12. An arrangement according to claim 11, comprising:
means for measuring at least one of curvature of an eye, thickness of a cornea of an eye and water content of an eye to form additional measurement information for determination of intraocular pressure information.

13. An arrangement according to claim 12, wherein a distance of said at least one recording location from said at least one generation location is known.

14. An arrangement according to claim 13, wherein the means for detecting surface vibrations is configured to detect a first arriving signal (FAS).

15. An arrangement according to claim 14, wherein the means for forming and directing laser radiation is configured to generate a mechanical wave by tuning at least one of centre frequency and pattern of the mechanical wave to facilitate an in vivo excitation through a surface of an eye.

16. An arrangement according to claim 11, wherein a distance of said at least one recording location from said at least one generation location is known.

17. An arrangement according to claim 11, wherein the means for detecting surface vibrations is configured to detect a first arriving signal (FAS).

18. An arrangement according to claim 11, wherein the means for forming and directing laser radiation is configured to generate a mechanical wave by tuning at least one of a centre frequency and pattern of the mechanical wave to facilitate an in vivo excitation through a surface of an eye.

* * * * *